US006180363B1

(12) United States Patent
Batard et al.

(10) Patent No.: US 6,180,363 B1
(45) Date of Patent: Jan. 30, 2001

(54) RECODING OF DNA SEQUENCES PERMITTING EXPRESSION IN YEAST AND OBTAINED TRANSFORMED YEAST

(75) Inventors: Yannick Batard, Strasbourg; Francis Durst, Bernolsheim; Michel Schalk, Hutteheim; Daniele Werck-Reichhart, Dingsheim, all of (FR)

(73) Assignee: Rhone-Poulenc Agro, Lyon Cede (FR)

( * ) Notice: Under 35 U.S.C. 154(b), the term of this patent shall be extended for 0 days.

(21) Appl. No.: 09/158,767

(22) Filed: Sep. 23, 1998

(30) Foreign Application Priority Data

Sep. 24, 1997 (FR) ..... 97-12094

(51) Int. Cl.[7] ..... C12P 21/02; C12P 19/34

(52) U.S. Cl. ..... 435/69.1; 435/91.1

(58) Field of Search ..... 536/23.1; 435/320.1, 435/254.2, 69.1

(56) References Cited

U.S. PATENT DOCUMENTS 5,096,825 3/1992 Barr et al. ..... 435/255

FOREIGN PATENT DOCUMENTS 0255233 2/1988 (EP) .
2216530 A 10/1989 (GB) .

OTHER PUBLICATIONS

Skaggs et al, Gene 169;105–109, 1996, Cloning and characterization of the Saccharomyces cerevisiae C–22 sterol desaturase gene, encoding a second cytochrome P–450 involved in ergosterol biosynthesis.*

Fang et al., J. Biol. Chem. 271: 16460–16465, 1996, The homologue of mammalian SPC12 is important for efficient signal peptidase activity in Saccharomyces cerevisiae.* http://www.kazusa.or.jp/codon/(Internet site for Codon Usage Database from Yasukasu Nakamura; accessed on Dec. 13, 1999).*

GenBank database entry with accession number X87611 Dec. 16, 1999 (found at internet site http://www.ncbi.nlm.nih.gov:80?entrez/; accessed on Dec. 13, 1999.*

Murray et al. (1989) *Nucleic Acids Research* 17:477.

* cited by examiner

*Primary Examiner*—Robert A. Schwartzman
*Assistant Examiner*—Katharine F Davis
(74) *Attorney, Agent, or Firm*—Baker Botts

(57) ABSTRACT

The present invention relates to a DNA sequence which encodes a protein of interest which contains regions having a high content of codons which are poorly suited to yeasts, characterized in that a sufficient number of codons which are poorly suited to yeasts is replaced with corresponding codons which are well-suited to yeasts in the said regions having a high content of codons which are poorly suited to yeasts. The present invention relates, more specifically, to DNA sequences which originate from dicotyledonous or monocotyledonous plants, in particular plants of the graminae family which are selected, in particular, from among wheat, barley, oats, rice, maize, sorghum and cane sugar. The present invention also relates to transformed yeasts which contain a DNA sequence according to the invention.

47 Claims, No Drawings

SEQUENCE LISTING

```
<160> NUMBER OF SEQ ID NOS: 20

<210> SEQ ID NO 1
<211> LENGTH: 2261
<212> TYPE: DNA
<213> ORGANISM: Triticum aestivum

<400> SEQUENCE: 1

cgcagcacgg caacacatac acaggagcca cacaccgcac ctaccccgat ggacgtcctc      60

ctcctggaga aggccctcct gggcctcttc gccgcggcgg tgctggccat cgccgtcgcc     120

aagctcaccg gcaagcgctt ccgcctcccc cctggcccct ccggcgcccc catcgtcggc     180

aactggctgc aggtcggcga cgacctcaac caccgcaacc tgatgggcct ggccaagcgg     240

ttcggcgagg tgttcctcct ccgcatgggc gtccgcaacc tggtggtcgt ctccagcccc     300

gagctcgcca aggaggtcct ccacacccag ggcgtcgagt tcggctcccg cacccgcaac     360
```

-continued

```
gtcgtcttcg acatcttcac cggcaaggga caggacatgg tgttcacggt gtacggcgac    420

cactggcgca agatgcggcg gatcatgacg gtgcccttct tcaccaacaa ggtggtggcg    480

cagaaccgcg tggggtggga ggaggaggcc cggctggtgg tggaggacct caaggccgac    540

ccggcggcgg cgacggcggg cgtggtggtc cgccgcaggc tgcagctcat gatgtacaac    600

gacatgttcc gcatcatgtt cgaccgccgg ttcgagagcg tggccgaccc gctcttcaac    660

cagctcaagg cgctcaacgc cgagcgcagc atcctctccc agagcttcga ctacaactac    720

ggcgacttca tccccgtcct ccgcccctc ctccgccgct acctcaaccg ctgcaccaac    780

ctcaagacca agcggatgaa ggtgttcgag gaccacttcg tccagcagcg caaggaggcg    840

ttggagaaga cgggtgagat caggtgcgcc atggaccaca tcctggaagc cgaaaggaag    900

ggcgagatca accacgacaa cgtcctctac atcgtcgaga acatcaacgt cgcagccatc    960

gagacgacgc tgtggtcgat cgagtggggc ctcgcggagc tggtgaacca cccggagatc   1020

cagcagaagc tgcgcgagga gatcgtcgcc gttctgggcg ccggcgtggc ggtgacggag   1080

ccggacctgg agcgcctccc ctacctgcag tccgtggtga aggagacgct ccgcctccgc   1140

atggcaatcc cgctcctggt gccgcacatg aacctcagcg acgccaagct cgccggctac   1200

gacatccccg ccgagtccaa gatcctcgtc aacgcctggt tcctcgccaa cgaccccaag   1260

cggtgggtgc gcgccgatga gttcaggccg gagaggttcc tcgaggagga gaaggccgtc   1320

gaggcccacg gcaacgattt ccggttcgtg cccttcggcg tcggccgccg gagctgcccc   1380

gggatcatcc tcgcgctgcc catcatcggc atcacgctcg gacgcctggt gcagaacttc   1440

cagctgctgc cgccgccggg gcaggacaag atcgacacca ccgagaagcc cgggcagttt   1500

accaaccaga tcctcaagca cgccaccatt gtctgcaagc cactcgaggc ttaactgaat   1560

tgaggtttcg gtcatgggcg cccgctgacg cggggagatg gatctatgca tgtgactgtg   1620

tattttgcct tctttctttt tggtgttgtt ttttgcagta gtaagtttaa tttttctttg   1680

gtgttggcct atttgtcttc atgtgaggcg tcgtgttgta aatttccata tagttggcaa   1740

tgtgatgtaa aacttggctc caaaaaaaaa aaaaaaaaac tcgagactct tctctctctc   1800

tctctctctc cagcctcggg tctctgctgg caagggaact tgcattaccc tgtgtacgac   1860

ggcgccatgt tcgtccctga agcaccctcc ctgcagagct cccaggacaa cttcgctgca   1920

tctgctggtt tcaagcgtcg aaggagagag ttttgaatac ccgaaagaat atagcgttgg   1980

acatatctgt caaacagggg atcttgctgt gggtctcttg gtgggccaaa tcgcatagac   2040

aatcattcaa atggatgggt tcttcgctgg tcggtcaaaa agtatatgtt gtaattgtac   2100

gcctttttttg ggtcttgttg ccaaagatca tggttattga gttgtgagct ctgagataac   2160

aggtttgtgt atagtgaaat aaagaggagc gtcgtcaaca ccatgtacta tataggcttt   2220

gaaattccat taagatgcat cagaaatcaa tgttggattt g                      2261


<210> SEQ ID NO 2
<211> LENGTH: 38
<212> TYPE: DNA
<213> ORGANISM: Artificial Sequence
<220> FEATURE:
<223> OTHER INFORMATION: Synthetic primer

<400> SEQUENCE: 2

atatatggat ccatggacgt cctcctcctg gagaaggc                             38


<210> SEQ ID NO 3
<211> LENGTH: 56
```

```
<212> TYPE: DNA
<213> ORGANISM: Artificial Sequence
<220> FEATURE:
<223> OTHER INFORMATION: Synthetic primer

<400> SEQUENCE: 3

atatatggat ccatggatgt tttgttgttg gagaaggccc tcctgggcct cttcgc        56


<210> SEQ ID NO 4
<211> LENGTH: 71
<212> TYPE: DNA
<213> ORGANISM: Triticum aestivum
<220> FEATURE:
<223> OTHER INFORMATION: Synthetic primer

<400> SEQUENCE: 4

atatatggat ccatggatgt tttgttgttg gaaaaagctt tgttgggttt gttcgccgcg     60

gcggtgctgg c                                                          71


<210> SEQ ID NO 5
<211> LENGTH: 143
<212> TYPE: DNA
<213> ORGANISM: Artificial Sequence
<220> FEATURE:
<223> OTHER INFORMATION: Synthetic primer

<400> SEQUENCE: 5

atatatggat ccatggatgt tttgttgttg gaaaaagctt tgttgggttt gtttgctgct     60

gctgttttgg ctattgctgt tgctaaattg actggtaaaa gatttagatt gccaccaggt    120

ccatccggcg cccccatcgt cgg                                            143


<210> SEQ ID NO 6
<211> LENGTH: 39
<212> TYPE: DNA
<213> ORGANISM: Artificial Sequence
<220> FEATURE:
<223> OTHER INFORMATION: Synthetic primer

<400> SEQUENCE: 6

tatatagaat tccagttaag cctcgagtgg cttgcagac                            39


<210> SEQ ID NO 7
<211> LENGTH: 1506
<212> TYPE: DNA
<213> ORGANISM: Artificial Sequence
<220> FEATURE:
<223> OTHER INFORMATION: Altered sequences

<400> SEQUENCE: 7

atggatgttt tgttgttgga gaaggccctc ctgggcctct tcgccgcggc ggtgctggcc     60

atcgccgtcg ccaagctcac cggcaagcgc ttccgcctcc cccctggccc ctccggcgcc    120

cccatcgtcg gcaactggct gcaggtcggc gacgacctca accaccgcaa cctgatgggc    180

ctggccaagc ggttcggcga ggtgttcctc ctccgcatgg gcgtccgcaa cctggtggtc    240

gtctccagcc ccgagctcgc caaggaggtc ctccacaccc agggcgtcga gttcggctcc    300

cgcacccgca acgtcgtctt cgacatcttc accggcaagg gacaggacat ggtgttcacg    360

gtgtacggcg accactggcg caagatgcgg cggatcatga cggtgccctt cttcaccaac    420

aaggtggtgg cgcagaaccg cgtggggtgg gaggaggagg cccggctggt ggtggaggac    480

ctcaaggccg acccggcggc ggcgacggcg ggcgtggtgg tccgccgcag gctgcagctc    540
```

-continued

```
atgatgtaca acgacatgtt ccgcatcatg ttcgaccgcc ggttcgagag cgtggccgac     600

ccgctcttca accagctcaa ggcgctcaac gccgagcgca gcatcctctc ccagagcttc     660

gactacaact acggcgactt catccccgtc ctccgcccct tcctccgccg ctacctcaac     720

cgctgcacca acctcaagac caagcggatg aaggtgttcg aggaccactt cgtccagcag     780

cgcaaggagg cgttggagaa gacgggtgag atcaggtgcg ccatggacca catcctggaa     840

gccgaaagga agggcgagat caaccacgac aacgtcctct acatcgtcga gaacatcaac     900

gtcgcagcca tcgagacgac gctgtggtcg atcgagtggg gcctcgcgga gctggtgaac     960

cacccggaga tccagcagaa gctgcgcgag gagatcgtcg ccgttctggg cgccggcgtg    1020

gcggtgacgg agccggacct ggagcgcctc ccctacctgc agtccgtggt gaaggagacg    1080

ctccgcctcc gcatggcaat cccgctcctg gtgccgcaca tgaacctcag cgacgccaag    1140

ctcgccggct acgacatccc cgccgagtcc aagatcctcg tcaacgcctg gttcctcgcc    1200

aacgacccca agcggtgggt gcgcgccgat gagttcaggc cggagaggtt cctcgaggag    1260

gagaaggccg tcgaggccca cggcaacgat ttccggttcg tgcccttcgg cgtcggccgc    1320

cggagctgcc ccgggatcat cctcgcgctg cccatcatcg gcatcacgct cggacgcctg    1380

gtgcagaact tccagctgct gccgccgccg gggcaggaca agatcgacac caccgagaag    1440

cccgggcagt ttaccaacca gatcctcaag cacgccacca ttgtctgcaa gccactcgag    1500

gcttaa                                                                1506


<210> SEQ ID NO 8
<211> LENGTH: 1506
<212> TYPE: DNA
<213> ORGANISM: Artificial Sequence
<220> FEATURE:
<223> OTHER INFORMATION: Altered sequences

<400> SEQUENCE: 8

atggatgttt tgttgttgga aaaagctttg ttgggtttgt tcgccgcggc ggtgctggcc      60

atcgccgtcg ccaagctcac cggcaagcgc ttccgcctcc cccctggccc ctccggcgcc     120

cccatcgtcg gcaactggct gcaggtcggc gacgacctca accaccgcaa cctgatgggc     180

ctggccaagc ggttcggcga ggtgttcctc ctccgcatgg gcgtccgcaa cctggtggtc     240

gtctccagcc ccgagctcgc caaggaggtc ctccacaccc agggcgtcga gttcggctcc     300

cgcacccgca acgtcgtctt cgacatcttc accggcaagg gacaggacat ggtgttcacg     360

gtgtacggcg accactggcg caagatgcgg cggatcatga cggtgccctt cttcaccaac     420

aaggtggtgg cgcagaaccg cgtggggtgg gaggaggagg cccggctggt ggtggaggac     480

ctcaaggccg acccggcggc ggcgacggcg ggcgtggtgg tccgccgcag gctgcagctc     540

atgatgtaca acgacatgtt ccgcatcatg ttcgaccgcc ggttcgagag cgtggccgac     600

ccgctcttca accagctcaa ggcgctcaac gccgagcgca gcatcctctc ccagagcttc     660

gactacaact acggcgactt catccccgtc ctccgcccct tcctccgccg ctacctcaac     720

cgctgcacca acctcaagac caagcggatg aaggtgttcg aggaccactt cgtccagcag     780

cgcaaggagg cgttggagaa gacgggtgag atcaggtgcg ccatggacca catcctggaa     840

gccgaaagga agggcgagat caaccacgac aacgtcctct acatcgtcga gaacatcaac     900

gtcgcagcca tcgagacgac gctgtggtcg atcgagtggg gcctcgcgga gctggtgaac     960

cacccggaga tccagcagaa gctgcgcgag gagatcgtcg ccgttctggg cgccggcgtg    1020

gcggtgacgg agccggacct ggagcgcctc ccctacctgc agtccgtggt gaaggagacg    1080
```

-continued

```
ctccgcctcc gcatggcaat cccgctcctg gtgccgcaca tgaacctcag cgacgccaag   1140

ctcgccggct acgacatccc cgccgagtcc aagatcctcg tcaacgcctg gttcctcgcc   1200

aacgacccca agcggtgggt gcgcgccgat gagttcaggc cggagaggtt cctcgaggag   1260

gagaaggccg tcgaggccca cggcaacgat ttccggttcg tgcccttcgg cgtcggccgc   1320

cggagctgcc ccgggatcat cctcgcgctg cccatcatcg gcatcacgct cggacgcctg   1380

gtgcagaact tccagctgct gccgccgccg gggcaggaca agatcgacac caccgagaag   1440

cccgggcagt ttaccaacca gatcctcaag cacgccacca ttgtctgcaa gccactcgag   1500

gcttaa                                                              1506
```

```
<210> SEQ ID NO 9
<211> LENGTH: 1506
<212> TYPE: DNA
<213> ORGANISM: Artificial Sequence
<220> FEATURE:
<223> OTHER INFORMATION: Altered sequences

<400> SEQUENCE: 9

atggatgttt tgttgttgga aaaagctttg ttgggtttgt ttgctgctgc tgttttggct     60

attgctgttg ctaaattgac tggtaaaaga tttagattgc caccaggtcc atccggcgcc    120

cccatcgtcg gcaactggct gcaggtcggc gacgacctca accaccgcaa cctgatgggc    180

ctggccaagc ggttcggcga ggtgttcctc ctccgcatgg gcgtccgcaa cctggtggtc    240

gtctccagcc ccgagctcgc caaggaggtc ctccacaccc agggcgtcga gttcggctcc    300

cgcacccgca acgtcgtctt cgacatcttc accggcaagg gacaggacat ggtgttcacg    360

gtgtacggcg accactggcg caagatgcgg cggatcatga cggtgccctt cttcaccaac    420

aaggtggtgg cgcagaaccg cgtggggtgg gaggaggagg cccggctggt ggtggaggac    480

ctcaaggccg acccggcggc ggcgacggcg ggcgtggtgg tccgccgcag gctgcagctc    540

atgatgtaca acgacatgtt ccgcatcatg ttcgaccgcc ggttcgagag cgtggccgac    600

ccgctcttca accagctcaa ggcgctcaac gccgagcgca gcatcctctc ccagagcttc    660

gactacaact acggcgactt catccccgtc ctccgcccct tcctccgccg ctacctcaac    720

cgctgcacca acctcaagac caagcggatg aaggtgttcg aggaccactt cgtccagcag    780

cgcaaggagg cgttggagaa gacgggtgag atcaggtgcg ccatggacca catcctggaa    840

gccgaaagga agggcgagat caaccacgac aacgtcctct acatcgtcga gaacatcaac    900

gtcgcagcca tcgagacgac gctgtggtcg atcgagtggg gcctcgcgga gctggtgaac    960

cacccggaga tccagcagaa gctgcgcgag gagatcgtcg ccgttctggg cgccggcgtg   1020

gcggtgacgg agccggacct ggagcgcctc ccctacctgc agtccgtggt gaaggagacg   1080

ctccgcctcc gcatggcaat cccgctcctg gtgccgcaca tgaacctcag cgacgccaag   1140

ctcgccggct acgacatccc cgccgagtcc aagatcctcg tcaacgcctg gttcctcgcc   1200

aacgacccca agcggtgggt gcgcgccgat gagttcaggc cggagaggtt cctcgaggag   1260

gagaaggccg tcgaggccca cggcaacgat ttccggttcg tgcccttcgg cgtcggccgc   1320

cggagctgcc ccgggatcat cctcgcgctg cccatcatcg gcatcacgct cggacgcctg   1380

gtgcagaact tccagctgct gccgccgccg gggcaggaca agatcgacac caccgagaag   1440

cccgggcagt ttaccaacca gatcctcaag cacgccacca ttgtctgcaa gccactcgag   1500

gcttaa                                                              1506
```

-continued

<210> SEQ ID NO 10
<211> LENGTH: 2181
<212> TYPE: DNA
<213> ORGANISM: Triticum aestivum

<400> SEQUENCE: 10

```
cgatccaccc cttggatcca ctctacccag ctcgctagcc agcggggtac atacacgcac     60

gcacgtacgc gcgtacgtac actcgcagag cttgcttcag ggaggccggc aatggaggtg    120

gggacgtggg cggtggtggt gtcggcggtg gccgcgtaca tggcgtggtt ctggcggatg    180

tcccgcgggc tgcgcgggcc gcgggtttgg cccgtgctcg gcagcctgcc gggcctggtg    240

cagcacgccg aggacatgca cgagtggatc gccggcaacc tgcgccgcgc gggcggcacg    300

taccagacct gcatcttcgc cgtgcccggg gtggcgcgcc gcggcggcct ggtcaccgtc    360

acctgcgacc cgcgcaacct ggagcacgtc ctgaaggcgc gcttcgacaa ctaccccaag    420

ggccccttct ggcacggcgt cttccgggac ctgctcggcg acggcatctt caattccgac    480

ggcgacacct ggctcgcgca gcgcaagacg gccgcgctcg agttcaccac ccgcacgctc    540

cggacggcca tgtcccgctg ggtctcgcgc tccatccacg gccgcctcct gcccatcctg    600

gccgacgcgg ccaagggcaa ggcgcaggtg gatctccagg acctcctcct ccgcctcacc    660

ttcgacaaca tctgcggcct ggccttcggc aaggacccgg agacgctcgc ccagggcctg    720

ccggagaacg agttcgcctc cgcgttcgac cgcgccaccg aggccacgct caaccgcttc    780

atcttcccgg agttcctgtg gcgctgcaaa aagtggctgg gcctcggcat ggagaccacg    840

ctgaccagca gcatggccca cgtcgaccag tacctcgccg ccgtcatcaa gaagcgcaag    900

ctcgagctcg ccgccggcaa cggcaaatgc gacacggcgg cgacgcacga cgacctgctc    960

tcccggttca tgcggaaggg ttcctactcg gacgagtcgc tccagcacgt ggcgctcaac   1020

ttcatcctcg ccggccgcga cacctcctcc gtggcgctct cctggttctt ctggctcgtg   1080

tccacccacc ctgcggtgga gcgcaagatc gtgcgcgagc tctgctccgt tctcgccgcg   1140

tcacggggcg cccatgaccc ggcattgtgg ctggcggagc ccttcacctt cgaggagctc   1200

gaccgcctgg tctacctcaa ggcggcgctg tcggagaccc tccgcctcta cccctccgtc   1260

cccgaggact ccaagcacgt cgtcgcggac gactacctcc ccgacggcac cttcgtgccg   1320

gccgggtcgt cggtcaccta ctccatatac tcggcggggc gcatgaaggg ggtgtggggg   1380

gaggactgcc tcgagttccg gccggagcga tggctgtcgg ccgacggcac caagttcgag   1440

cagcacgact cgtacaagtt cgtggcgttc aacgccgggc cgagggtgtg cctgggcaag   1500

gacctagcct acctgcagat gaagaacatc gccgggagcg tgctgctccg gcaccgcctg   1560

accgtggcgc cgggccaccg cgtggagcag aagatgtcgc tcacgctctt catgaagggc   1620

gggctacgga tggaggtacg tccgcgcgac ctcgcccccg tcctcgacga gccctgcggc   1680

ctggacgccg gcgccgccac cgccgccgca gcaagtgcca cagcgccgtg cgcgtagaag   1740

acctggcacc ggcacgcgcc atgcatgatt cgtgcgtgct agctgttgaa gggacgccgg   1800

acattgaatg tgtagatagg gcagcagtgc aagaccgtaa gtaaaattga tgatgggttt   1860

ggtgacaaca ttgaagccac tcctttccag aatttacgac ccggatagga gaaacaggga   1920

aactttgcag atcacaacac aagatctagc cagccgggga tctgatctga tttgcgtctg   1980

ctcggagcac gggtgcatgg gagaccaagg aggaaaacaa aaaataacag aaacagagtg   2040

agcaatattt gtgattgtag ccacgggaaa gagagaggag taattagtaa ttcagatttg   2100

tttgcagtag ctcggtgttg gtgaccagat catagccaac taggctattc tattctattc   2160
```

-continued tatttttgaa gatgattttt c 2181

<210> SEQ ID NO 11
<211> LENGTH: 39
<212> TYPE: DNA
<213> ORGANISM: Artificial Sequence
<220> FEATURE:
<223> OTHER INFORMATION: Synthetic primer

<400> SEQUENCE: 11
atatatggat ccatggaggt ggggacgtgg gcggtggtg 39

<210> SEQ ID NO 12
<211> LENGTH: 150
<212> TYPE: DNA
<213> ORGANISM: Artificial Sequence
<220> FEATURE:
<223> OTHER INFORMATION: Synthetic primer

<400> SEQUENCE: 12
atatatggat ccatggaagt tggtacttgg gctgttgttg tttctgctgt tgctgcttat 60
atggcttggt tttggagaat gtctagaggt ttgagaggtc caagagtttg gccagttttg 120
ggttctttgc caggcctggt gcagcacgcc 150

<210> SEQ ID NO 13
<211> LENGTH: 42
<212> TYPE: DNA
<213> ORGANISM: Artificial Sequence
<220> FEATURE:
<223> OTHER INFORMATION: Synthetic primer

<400> SEQUENCE: 13
tatatagaat tccttctacg cgcacggcgc tgtggcactt gc 42

<210> SEQ ID NO 14
<211> LENGTH: 1626
<212> TYPE: DNA
<213> ORGANISM: Artificial Sequence
<220> FEATURE:
<223> OTHER INFORMATION: Altered sequences

<400> SEQUENCE: 14
atggaagttg gtacttgggc tgttgttgtt tctgctgttg ctgcttatat ggcttggttt 60
tggagaatgt ctagaggttt gagaggtcca agagtttggc cagttttggg ttctttgcca 120
ggcctggtgc agcacgccga ggacatgcac gagtggatcg ccggcaacct gcgccgcgcg 180
ggcggcacgt accagacctg catcttcgcc gtgcccgggg tggcgcgccg cggcggcctg 240
gtcaccgtca cctgcgaccc gcgcaacctg gagcacgtcc tgaaggcgcg cttcgacaac 300
taccccaagg gccccttctg gcacggcgtc ttccgggacc tgctcggcga cggcatcttc 360
aattccgacg gcgacacctg gctcgcgcag cgcaagacgg ccgcgctcga gttcaccacc 420
cgcacgctcc ggacggccat gtcccgctgg gtctcgcgct ccatccacgg ccgcctcctg 480
cccatcctgg ccgacgcggc caagggcaag gcgcaggtgg atctccagga cctcctcctc 540
cgcctcacct tcgacaacat ctgcggcctg gccttcggca aggacccgga gacgctcgcc 600
cagggcctgc cggagaacga gttcgcctcc gcgttcgacc gcgccaccga ggccacgctc 660
aaccgcttca tcttcccgga gttcctgtgg cgctgcaaaa agtggctggg cctcggcatg 720
gagaccacgc tgaccagcag catggcccac gtcgaccagt acctcgccgc cgtcatcaag 780

-continued

```
aagcgcaagc tcgagctcgc cgccggcaac ggcaaatgcg acacggcggc gacgcacgac    840

gacctgctct cccggttcat gcggaagggt tcctactcgg acgagtcgct ccagcacgtg    900

gcgctcaact tcatcctcgc cggccgcgac acctcctccg tggcgctctc ctggttcttc    960

tggctcgtgt ccacccaccc tgcggtggag cgcaagatcg tgcgcgagct ctgctccgtt   1020

ctcgccgcgt cacggggcgc ccatgacccg gcattgtggc tggcggagcc cttcaccttc   1080

gaggagctcg accgcctggt ctacctcaag gcggcgctgt cggagaccct ccgcctctac   1140

ccctccgtcc ccgaggactc caagcacgtc gtcgcggacg actacctccc cgacggcacc   1200

ttcgtgccgg ccgggtcgtc ggtcacctac tccatatact cggcggggcg catgaagggg   1260

gtgtgggggg aggactgcct cgagttccgg ccggagcgat ggctgtcggc cgacggcacc   1320

aagttcgagc agcacgactc gtacaagttc gtggcgttca acgccgggcc gagggtgtgc   1380

ctgggcaagg acctagccta cctgcagatg aagaacatcg ccgggagcgt gctgctccgg   1440

caccgcctga ccgtggcgcc gggccaccgc gtggagcaga agatgtcgct cacgctcttc   1500

atgaagggcg ggctacggat ggaggtacgt ccgcgcgacc tcgcccccgt cctcgacgag   1560

ccctgcggcc tggacgccgg cgccgccacc gccgccgcag caagtgccac agcgccgtgc   1620

gcgtag                                                              1626
```

<210> SEQ ID NO 15
<211> LENGTH: 501
<212> TYPE: PRT
<213> ORGANISM: Artificial Sequence
<220> FEATURE:
<223> OTHER INFORMATION: Altered sequences

<400> SEQUENCE: 15

```
Met Asp Val Leu Leu Leu Glu Lys Ala Leu Leu Gly Leu Phe Ala Ala
 1               5                  10                  15

Ala Val Leu Ala Ile Ala Val Ala Lys Leu Thr Gly Lys Arg Phe Arg
            20                  25                  30

Leu Pro Pro Gly Pro Ser Gly Ala Pro Ile Val Gly Asn Trp Leu Gln
        35                  40                  45

Val Gly Asp Asp Leu Asn His Arg Asn Leu Met Gly Leu Ala Lys Arg
    50                  55                  60

Phe Gly Glu Val Phe Leu Leu Arg Met Gly Val Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Asp His Trp Arg Lys
        115                 120                 125

Met Arg Arg Ile Met Thr Val Pro Phe Phe Thr Asn Lys Val Val Ala
    130                 135                 140

Gln Asn Arg Val Gly Trp Glu Glu Glu Ala Arg Leu Val Val Glu Asp
145                 150                 155                 160

Leu Lys Ala Asp Pro Ala Ala Ala Thr Ala Gly Val Val Val Arg Arg
                165                 170                 175

Arg Leu Gln Leu Met Met Tyr Asn Asp Met Phe Arg Ile Met Phe Asp
            180                 185                 190

Arg Arg Phe Glu Ser Val Ala Asp Pro Leu Phe Asn Gln Leu Lys Ala
        195                 200                 205
```

-continued

```
Leu Asn Ala Glu Arg Ser Ile Leu Ser Gln Ser Phe Asp Tyr Asn Tyr
    210                 215                 220

Gly Asp Phe Ile Pro Val Leu Arg Pro Phe Leu Arg Arg Tyr Leu Asn
225                 230                 235                 240

Arg Cys Thr Asn Leu Lys Thr Lys Arg Met Lys Val Phe Glu Asp His
                245                 250                 255

Phe Val Gln Gln Arg Lys Glu Ala Leu Glu Lys Thr Gly Glu Ile Arg
            260                 265                 270

Cys Ala Met Asp His Ile Leu Glu Ala Glu Arg Lys Gly Glu Ile Asn
        275                 280                 285

His Asp Asn Val Leu Tyr Ile Val Glu Asn Ile Asn Val Ala Ala Ile
    290                 295                 300

Glu Thr Thr Leu Trp Ser Ile Glu Trp Gly Leu Ala Glu Leu Val Asn
305                 310                 315                 320

His Pro Glu Ile Gln Gln Lys Leu Arg Glu Glu Ile Val Ala Val Leu
                325                 330                 335

Gly Ala Gly Val Ala Val Thr Glu Pro Asp Leu Glu Arg Leu Pro Tyr
            340                 345                 350

Leu Gln Ser Val Val Lys Glu Thr Leu Arg Leu Arg Met Ala Ile Pro
        355                 360                 365

Leu Leu Val Pro His Met Asn Leu Ser Asp Ala Lys Leu Ala Gly Tyr
    370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Ala Asp Glu Phe Arg Pro Glu Arg
                405                 410                 415

Phe Leu Glu Glu Glu Lys Ala Val Glu Ala His Gly Asn Asp Phe Arg
            420                 425                 430

Phe Val Pro Phe Gly Val Gly Arg Arg Ser Cys Pro Gly Ile Ile Leu
        435                 440                 445

Ala Leu Pro Ile Ile Gly Ile Thr Leu Gly Arg Leu Val Gln Asn Phe
    450                 455                 460

Gln Leu Leu Pro Pro Pro Gly Gln Asp Lys Ile Asp Thr Thr Glu Lys
465                 470                 475                 480

Pro Gly Gln Phe Thr Asn Gln Ile Leu Lys His Ala Thr Ile Val Cys
                485                 490                 495

Lys Pro Leu Glu Ala
            500


<210> SEQ ID NO 16
<211> LENGTH: 501
<212> TYPE: PRT
<213> ORGANISM: Artificial Sequence
<220> FEATURE:
<223> OTHER INFORMATION: Altered sequences

<400> SEQUENCE: 16

Met Asp Val Leu Leu Leu Glu Lys Ala Leu Leu Gly Leu Phe Ala Ala
 1               5                  10                  15

Ala Val Leu Ala Ile Ala Val Ala Lys Leu Thr Gly Lys Arg Phe Arg
            20                  25                  30

Leu Pro Pro Gly Pro Ser Gly Ala Pro Ile Val Gly Asn Trp Leu Gln
        35                  40                  45

Val Gly Asp Asp Leu Asn His Arg Asn Leu Met Gly Leu Ala Lys Arg
    50                  55                  60
```

-continued

```
Phe Gly Glu Val Phe Leu Leu Arg Met Gly Val Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Asp His Trp Arg Lys
        115                 120                 125

Met Arg Arg Ile Met Thr Val Pro Phe Phe Thr Asn Lys Val Val Ala
    130                 135                 140

Gln Asn Arg Val Gly Trp Glu Glu Glu Ala Arg Leu Val Val Glu Asp
145                 150                 155                 160

Leu Lys Ala Asp Pro Ala Ala Ala Thr Ala Gly Val Val Val Arg Arg
                165                 170                 175

Arg Leu Gln Leu Met Met Tyr Asn Asp Met Phe Arg Ile Met Phe Asp
            180                 185                 190

Arg Arg Phe Glu Ser Val Ala Asp Pro Leu Phe Asn Gln Leu Lys Ala
        195                 200                 205

Leu Asn Ala Glu Arg Ser Ile Leu Ser Gln Ser Phe Asp Tyr Asn Tyr
    210                 215                 220

Gly Asp Phe Ile Pro Val Leu Arg Pro Phe Leu Arg Arg Tyr Leu Asn
225                 230                 235                 240

Arg Cys Thr Asn Leu Lys Thr Lys Arg Met Lys Val Phe Glu Asp His
                245                 250                 255

Phe Val Gln Gln Arg Lys Glu Ala Leu Glu Lys Thr Gly Glu Ile Arg
            260                 265                 270

Cys Ala Met Asp His Ile Leu Glu Ala Glu Arg Lys Gly Glu Ile Asn
        275                 280                 285

His Asp Asn Val Leu Tyr Ile Val Glu Asn Ile Asn Val Ala Ala Ile
    290                 295                 300

Glu Thr Thr Leu Trp Ser Ile Glu Trp Gly Leu Ala Glu Leu Val Asn
305                 310                 315                 320

His Pro Glu Ile Gln Gln Lys Leu Arg Glu Glu Ile Val Ala Val Leu
                325                 330                 335

Gly Ala Gly Val Ala Val Thr Glu Pro Asp Leu Glu Arg Leu Pro Tyr
            340                 345                 350

Leu Gln Ser Val Val Lys Glu Thr Leu Arg Leu Arg Met Ala Ile Pro
        355                 360                 365

Leu Leu Val Pro His Met Asn Leu Ser Asp Ala Lys Leu Ala Gly Tyr
    370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Ala Asp Glu Phe Arg Pro Glu Arg
                405                 410                 415

Phe Leu Glu Glu Glu Lys Ala Val Glu Ala His Gly Asn Asp Phe Arg
            420                 425                 430

Phe Val Pro Phe Gly Val Gly Arg Arg Ser Cys Pro Gly Ile Ile Leu
        435                 440                 445

Ala Leu Pro Ile Ile Gly Ile Thr Leu Gly Arg Leu Val Gln Asn Phe
    450                 455                 460

Gln Leu Leu Pro Pro Pro Gly Gln Asp Lys Ile Asp Thr Thr Glu Lys
465                 470                 475                 480

Pro Gly Gln Phe Thr Asn Gln Ile Leu Lys His Ala Thr Ile Val Cys
```

-continued

```
                485                 490                 495

Lys Pro Leu Glu Ala
            500


<210> SEQ ID NO 17
<211> LENGTH: 501
<212> TYPE: PRT
<213> ORGANISM: Artificial Sequence
<220> FEATURE:
<223> OTHER INFORMATION: Altered sequences

<400> SEQUENCE: 17

Met Asp Val Leu Leu Leu Glu Lys Ala Leu Leu Gly Leu Phe Ala Ala
 1               5                  10                  15

Ala Val Leu Ala Ile Ala Val Ala Lys Leu Thr Gly Lys Arg Phe Arg
            20                  25                  30

Leu Pro Pro Gly Pro Ser Gly Ala Pro Ile Val Gly Asn Trp Leu Gln
        35                  40                  45

Val Gly Asp Asp Leu Asn His Arg Asn Leu Met Gly Leu Ala Lys Arg
    50                  55                  60

Phe Gly Glu Val Phe Leu Leu Arg Met Gly Val Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Asp His Trp Arg Lys
        115                 120                 125

Met Arg Arg Ile Met Thr Val Pro Phe Phe Thr Asn Lys Val Val Ala
    130                 135                 140

Gln Asn Arg Val Gly Trp Glu Glu Glu Ala Arg Leu Val Val Glu Asp
145                 150                 155                 160

Leu Lys Ala Asp Pro Ala Ala Ala Thr Ala Gly Val Val Val Arg Arg
                165                 170                 175

Arg Leu Gln Leu Met Met Tyr Asn Asp Met Phe Arg Ile Met Phe Asp
            180                 185                 190

Arg Arg Phe Glu Ser Val Ala Asp Pro Leu Phe Asn Gln Leu Lys Ala
        195                 200                 205

Leu Asn Ala Glu Arg Ser Ile Leu Ser Gln Ser Phe Asp Tyr Asn Tyr
    210                 215                 220

Gly Asp Phe Ile Pro Val Leu Arg Pro Phe Leu Arg Arg Tyr Leu Asn
225                 230                 235                 240

Arg Cys Thr Asn Leu Lys Thr Lys Arg Met Lys Val Phe Glu Asp His
                245                 250                 255

Phe Val Gln Gln Arg Lys Glu Ala Leu Glu Lys Thr Gly Glu Ile Arg
            260                 265                 270

Cys Ala Met Asp His Ile Leu Glu Ala Glu Arg Lys Gly Glu Ile Asn
        275                 280                 285

His Asp Asn Val Leu Tyr Ile Val Glu Asn Ile Asn Val Ala Ala Ile
    290                 295                 300

Glu Thr Thr Leu Trp Ser Ile Glu Trp Gly Leu Ala Glu Leu Val Asn
305                 310                 315                 320

His Pro Glu Ile Gln Gln Lys Leu Arg Glu Glu Ile Val Ala Val Leu
                325                 330                 335

Gly Ala Gly Val Ala Val Thr Glu Pro Asp Leu Glu Arg Leu Pro Tyr
```

-continued

```
            340                 345                 350

Leu Gln Ser Val Val Lys Glu Thr Leu Arg Leu Arg Met Ala Ile Pro
        355                 360                 365

Leu Leu Val Pro His Met Asn Leu Ser Asp Ala Lys Leu Ala Gly Tyr
    370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Ala Asp Glu Phe Arg Pro Glu Arg
                405                 410                 415

Phe Leu Glu Glu Glu Lys Ala Val Glu Ala His Gly Asn Asp Phe Arg
            420                 425                 430

Phe Val Pro Phe Gly Val Gly Arg Arg Ser Cys Pro Gly Ile Ile Leu
        435                 440                 445

Ala Leu Pro Ile Ile Gly Ile Thr Leu Gly Arg Leu Val Gln Asn Phe
    450                 455                 460

Gln Leu Leu Pro Pro Pro Gly Gln Asp Lys Ile Asp Thr Thr Glu Lys
465                 470                 475                 480

Pro Gly Gln Phe Thr Asn Gln Ile Leu Lys His Ala Thr Ile Val Cys
                485                 490                 495

Lys Pro Leu Glu Ala
            500


<210> SEQ ID NO 18
<211> LENGTH: 501
<212> TYPE: PRT
<213> ORGANISM: Artificial Sequence
<220> FEATURE:
<223> OTHER INFORMATION: Altered sequences

<400> SEQUENCE: 18

Met Asp Val Leu Leu Leu Glu Lys Ala Leu Leu Gly Leu Phe Ala Ala
 1               5                  10                  15

Ala Val Leu Ala Ile Ala Val Ala Lys Leu Thr Gly Lys Arg Phe Arg
            20                  25                  30

Leu Pro Pro Gly Pro Ser Gly Ala Pro Ile Val Gly Asn Trp Leu Gln
        35                  40                  45

Val Gly Asp Asp Leu Asn His Arg Asn Leu Met Gly Leu Ala Lys Arg
    50                  55                  60

Phe Gly Glu Val Phe Leu Leu Arg Met Gly Val Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Asp His Trp Arg Lys
        115                 120                 125

Met Arg Arg Ile Met Thr Val Pro Phe Phe Thr Asn Lys Val Val Ala
    130                 135                 140

Gln Asn Arg Val Gly Trp Glu Glu Glu Ala Arg Leu Val Val Glu Asp
145                 150                 155                 160

Leu Lys Ala Asp Pro Ala Ala Ala Thr Ala Gly Val Val Val Arg Arg
                165                 170                 175

Arg Leu Gln Leu Met Met Tyr Asn Asp Met Phe Arg Ile Met Phe Asp
            180                 185                 190

Arg Arg Phe Glu Ser Val Ala Asp Pro Leu Phe Asn Gln Leu Lys Ala
```

-continued

```
        195                 200                 205

Leu Asn Ala Glu Arg Ser Ile Leu Ser Gln Ser Phe Asp Tyr Asn Tyr
    210                 215                 220

Gly Asp Phe Ile Pro Val Leu Arg Pro Phe Leu Arg Arg Tyr Leu Asn
225                 230                 235                 240

Arg Cys Thr Asn Leu Lys Thr Lys Arg Met Lys Val Phe Glu Asp His
                245                 250                 255

Phe Val Gln Gln Arg Lys Glu Ala Leu Glu Lys Thr Gly Glu Ile Arg
            260                 265                 270

Cys Ala Met Asp His Ile Leu Glu Ala Glu Arg Lys Gly Glu Ile Asn
        275                 280                 285

His Asp Asn Val Leu Tyr Ile Val Glu Asn Ile Asn Val Ala Ala Ile
    290                 295                 300

Glu Thr Thr Leu Trp Ser Ile Glu Trp Gly Leu Ala Glu Leu Val Asn
305                 310                 315                 320

His Pro Glu Ile Gln Gln Lys Leu Arg Glu Glu Ile Val Ala Val Leu
                325                 330                 335

Gly Ala Gly Val Ala Val Thr Glu Pro Asp Leu Glu Arg Leu Pro Tyr
            340                 345                 350

Leu Gln Ser Val Val Lys Glu Thr Leu Arg Leu Arg Met Ala Ile Pro
        355                 360                 365

Leu Leu Val Pro His Met Asn Leu Ser Asp Ala Lys Leu Ala Gly Tyr
    370                 375                 380

Asp Ile Pro Ala Glu Ser Lys Ile Leu Val Asn Ala Trp Phe Leu Ala
385                 390                 395                 400

Asn Asp Pro Lys Arg Trp Val Arg Ala Asp Glu Phe Arg Pro Glu Arg
                405                 410                 415

Phe Leu Glu Glu Lys Ala Val Glu Ala His Gly Asn Asp Phe Arg
            420                 425                 430

Phe Val Pro Phe Gly Val Gly Arg Arg Ser Cys Pro Gly Ile Ile Leu
        435                 440                 445

Ala Leu Pro Ile Ile Gly Ile Thr Leu Gly Arg Leu Val Gln Asn Phe
    450                 455                 460

Gln Leu Leu Pro Pro Pro Gly Gln Asp Lys Ile Asp Thr Thr Glu Lys
465                 470                 475                 480

Pro Gly Gln Phe Thr Asn Gln Ile Leu Lys His Ala Thr Ile Val Cys
                485                 490                 495

Lys Pro Leu Glu Ala
            500


<210> SEQ ID NO 19
<211> LENGTH: 541
<212> TYPE: PRT
<213> ORGANISM: Artificial Sequence
<220> FEATURE:
<223> OTHER INFORMATION: Altered sequences

<400> SEQUENCE: 19

Met Glu Val Gly Thr Trp Ala Val Val Val Ser Ala Val Ala Ala Tyr
 1               5                  10                  15

Met Ala Trp Phe Trp Arg Met Ser Arg Gly Leu Arg Gly Pro Arg Val
            20                  25                  30

Trp Pro Val Leu Gly Ser Leu Pro Gly Leu Val Gln His Ala Glu Asp
        35                  40                  45

Met His Glu Trp Ile Ala Gly Asn Leu Arg Arg Ala Gly Gly Thr Tyr
```

-continued

```
    50                  55                  60

Gln Thr Cys Ile Phe Ala Val Pro Gly Val Ala Arg Arg Gly Gly Leu
65                  70                  75                  80

Val Thr Val Thr Cys Asp Pro Arg Asn Leu Glu His Val Leu Lys Ala
                85                  90                  95

Arg Phe Asp Asn Tyr Pro Lys Gly Pro Phe Trp His Gly Val Phe Arg
            100                 105                 110

Asp Leu Leu Gly Asp Gly Ile Phe Asn Ser Asp Gly Asp Thr Trp Leu
        115                 120                 125

Ala Gln Arg Lys Thr Ala Ala Leu Glu Phe Thr Thr Arg Thr Leu Arg
    130                 135                 140

Thr Ala Met Ser Arg Trp Val Ser Arg Ser Ile His Gly Arg Leu Leu
145                 150                 155                 160

Pro Ile Leu Ala Asp Ala Ala Lys Gly Lys Ala Gln Val Asp Leu Gln
                165                 170                 175

Asp Leu Leu Leu Arg Leu Thr Phe Asp Asn Ile Cys Gly Leu Ala Phe
            180                 185                 190

Gly Lys Asp Pro Glu Thr Leu Ala Gln Gly Leu Pro Glu Asn Glu Phe
        195                 200                 205

Ala Ser Ala Phe Asp Arg Ala Thr Glu Ala Thr Leu Asn Arg Phe Ile
    210                 215                 220

Phe Pro Glu Phe Leu Trp Arg Cys Lys Lys Trp Leu Gly Leu Gly Met
225                 230                 235                 240

Glu Thr Thr Leu Thr Ser Ser Met Ala His Val Asp Gln Tyr Leu Ala
                245                 250                 255

Ala Val Ile Lys Lys Arg Lys Leu Glu Leu Ala Ala Gly Asn Gly Lys
            260                 265                 270

Cys Asp Thr Ala Ala Thr His Asp Asp Leu Leu Ser Arg Phe Met Arg
        275                 280                 285

Lys Gly Ser Tyr Ser Asp Glu Ser Leu Gln His Val Ala Leu Asn Phe
    290                 295                 300

Ile Leu Ala Gly Arg Asp Thr Ser Ser Val Ala Leu Ser Trp Phe Phe
305                 310                 315                 320

Trp Leu Val Ser Thr His Pro Ala Val Glu Arg Lys Ile Val Arg Glu
                325                 330                 335

Leu Cys Ser Val Leu Ala Ala Ser Arg Gly Ala His Asp Pro Ala Leu
            340                 345                 350

Trp Leu Ala Glu Pro Phe Thr Phe Glu Glu Leu Asp Arg Leu Val Tyr
        355                 360                 365

Leu Lys Ala Ala Leu Ser Glu Thr Leu Arg Leu Tyr Pro Ser Val Pro
    370                 375                 380

Glu Asp Ser Lys His Val Val Ala Asp Asp Tyr Leu Pro Asp Gly Thr
385                 390                 395                 400

Phe Val Pro Ala Gly Ser Ser Val Thr Tyr Ser Ile Tyr Ser Ala Gly
                405                 410                 415

Arg Met Lys Gly Val Trp Gly Glu Asp Cys Leu Glu Phe Arg Pro Glu
            420                 425                 430

Arg Trp Leu Ser Ala Asp Gly Thr Lys Phe Glu Gln His Asp Ser Tyr
        435                 440                 445

Lys Phe Val Ala Phe Asn Ala Gly Pro Arg Val Cys Leu Gly Lys Asp
    450                 455                 460

Leu Ala Tyr Leu Gln Met Lys Asn Ile Ala Gly Ser Val Leu Leu Arg
465                 470                 475                 480
```

-continued

```
His Arg Leu Thr Val Ala Pro Gly His Arg Val Glu Gln Lys Met Ser
                485                 490                 495

Leu Thr Leu Phe Met Lys Gly Gly Leu Arg Met Glu Val Arg Pro Arg
            500                 505                 510

Asp Leu Ala Pro Val Leu Asp Glu Pro Cys Gly Leu Asp Ala Gly Ala
        515                 520                 525

Ala Thr Ala Ala Ala Ala Ser Ala Thr Ala Pro Cys Ala
    530                 535                 540


<210> SEQ ID NO 20
<211> LENGTH: 541
<212> TYPE: PRT
<213> ORGANISM: Artificial Sequence
<220> FEATURE:
<223> OTHER INFORMATION: Altered sequences

<400> SEQUENCE: 20

Met Glu Val Gly Thr Trp Ala Val Val Val Ser Ala Val Ala Ala Tyr
 1               5                  10                  15

Met Ala Trp Phe Trp Arg Met Ser Arg Gly Leu Arg Gly Pro Arg Val
            20                  25                  30

Trp Pro Val Leu Gly Ser Leu Pro Gly Leu Val Gln His Ala Glu Asp
        35                  40                  45

Met His Glu Trp Ile Ala Gly Asn Leu Arg Arg Ala Gly Gly Thr Tyr
    50                  55                  60

Gln Thr Cys Ile Phe Ala Val Pro Gly Val Ala Arg Arg Gly Gly Leu
65                  70                  75                  80

Val Thr Val Thr Cys Asp Pro Arg Asn Leu Glu His Val Leu Lys Ala
                85                  90                  95

Arg Phe Asp Asn Tyr Pro Lys Gly Pro Phe Trp His Gly Val Phe Arg
            100                 105                 110

Asp Leu Leu Gly Asp Gly Ile Phe Asn Ser Asp Gly Asp Thr Trp Leu
        115                 120                 125

Ala Gln Arg Lys Thr Ala Ala Leu Glu Phe Thr Thr Arg Thr Leu Arg
    130                 135                 140

Thr Ala Met Ser Arg Trp Val Ser Arg Ser Ile His Gly Arg Leu Leu
145                 150                 155                 160

Pro Ile Leu Ala Asp Ala Ala Lys Gly Lys Ala Gln Val Asp Leu Gln
                165                 170                 175

Asp Leu Leu Leu Arg Leu Thr Phe Asp Asn Ile Cys Gly Leu Ala Phe
            180                 185                 190

Gly Lys Asp Pro Glu Thr Leu Ala Gln Gly Leu Pro Glu Asn Glu Phe
        195                 200                 205

Ala Ser Ala Phe Asp Arg Ala Thr Glu Ala Thr Leu Asn Arg Phe Ile
    210                 215                 220

Phe Pro Glu Phe Leu Trp Arg Cys Lys Lys Trp Leu Gly Leu Gly Met
225                 230                 235                 240

Glu Thr Thr Leu Thr Ser Ser Met Ala His Val Asp Gln Tyr Leu Ala
                245                 250                 255

Ala Val Ile Lys Lys Arg Lys Leu Glu Leu Ala Ala Gly Asn Gly Lys
            260                 265                 270

Cys Asp Thr Ala Ala Thr His Asp Asp Leu Leu Ser Arg Phe Met Arg
        275                 280                 285

Lys Gly Ser Tyr Ser Asp Glu Ser Leu Gln His Val Ala Leu Asn Phe
    290                 295                 300
```

-continued

```
Ile Leu Ala Gly Arg Asp Thr Ser Ser Val Ala Leu Ser Trp Phe Phe
305                 310                 315                 320

Trp Leu Val Ser Thr His Pro Ala Val Glu Arg Lys Ile Val Arg Glu
                325                 330                 335

Leu Cys Ser Val Leu Ala Ala Ser Arg Gly Ala His Asp Pro Ala Leu
            340                 345                 350

Trp Leu Ala Glu Pro Phe Thr Phe Glu Glu Leu Asp Arg Leu Val Tyr
        355                 360                 365

Leu Lys Ala Ala Leu Ser Glu Thr Leu Arg Leu Tyr Pro Ser Val Pro
    370                 375                 380

Glu Asp Ser Lys His Val Val Ala Asp Asp Tyr Leu Pro Asp Gly Thr
385                 390                 395                 400

Phe Val Pro Ala Gly Ser Ser Val Thr Tyr Ser Ile Tyr Ser Ala Gly
                405                 410                 415

Arg Met Lys Gly Val Trp Gly Glu Asp Cys Leu Glu Phe Arg Pro Glu
            420                 425                 430

Arg Trp Leu Ser Ala Asp Gly Thr Lys Phe Glu Gln His Asp Ser Tyr
        435                 440                 445

Lys Phe Val Ala Phe Asn Ala Gly Pro Arg Val Cys Leu Gly Lys Asp
    450                 455                 460

Leu Ala Tyr Leu Gln Met Lys Asn Ile Ala Gly Ser Val Leu Leu Arg
465                 470                 475                 480

His Arg Leu Thr Val Ala Pro Gly His Arg Val Glu Gln Lys Met Ser
                485                 490                 495

Leu Thr Leu Phe Met Lys Gly Gly Leu Arg Met Glu Val Arg Pro Arg
            500                 505                 510

Asp Leu Ala Pro Val Leu Asp Glu Pro Cys Gly Leu Asp Ala Gly Ala
        515                 520                 525

Ala Thr Ala Ala Ala Ala Ser Ala Thr Ala Pro Cys Ala
    530                 535                 540
```

RECODING OF DNA SEQUENCES PERMITTING EXPRESSION IN YEAST AND OBTAINED TRANSFORMED YEAST

The present invention relates to the recoding of DNA sequences which encode proteins which contain regions having a high content of codons which are poorly translated by yeasts, in particular which encode proteins of plant origin, such as the P450 cytochromes of plant origin, and to their expression in yeasts.

It is known that certain sequences encoding proteins of interest, in particular proteins of plant origin, are not readily translated in yeasts. This applies, in particular, to proteins which possess regions having a high content of codons which are poorly suited to yeasts, in particular leucine codons, such as some P450 cytochromes of plant origin. Some systems which have been developed for improving the expression of P450 cytochromes of animal or plant origin in yeasts, such as those described by Pompon et al. (*Methods Enzymol.*, 272, 1996, 51–64; WO 97/10344), have turned out to be unsuitable for large numbers of P450 cytochromes which encompass regions having a high content of codons which are poorly suited to yeasts.

The P450 cytochromes constitute a superfamily of membrane enzymes of the monooxygenase type which are able to oxidize a large family of generally hydrophobic substrates. The reactions are most frequently characterized by the oxidation of C—H or C═C bonds, and of heteroatoms, and, more rarely, by the reduction of nitro groups or by dehalogenation. More specifically, these enzymes are involved in the metabolism of xenobiotic substances and drugs and in the biosynthesis of secondary metabolites in plants, some of which have organoleptic or pharmacodynamic properties.

As a consequence, the P450 cytochromes are used, in particular, in:

- the in vitro diagnosis of the formation of toxic or mutagenic metabolites (molecules of natural origin, pollutants, drugs, pesticides, etc.), making it possible, in particular, to develop novel active molecules (pharmaceutical, agrochemistry),
- the identification and destruction of molecules which are toxic for, or pollute, the environment,
- the enzymic synthesis of novel molecules.

The search for heterologous expression of P450 cytochromes by host cells, more specifically yeasts, is therefore important for obtaining controlled production of this enzyme in large quantity, either for isolating it and using it in the above-listed processes, or for using the transformed cells directly for the said processes without previously isolating the enzyme.

The present invention provides a solution to the above-mentioned problem, enabling proteins which contain regions having a high content of codons which are poorly suited to yeasts, in particular P450 cytochromes of plant origin, to be expressed in yeasts.

The present invention therefore relates to a DNA sequence, in particular a cDNA sequence, which encodes a protein of interest which contains regions having a high content of codons which are poorly suited to yeasts, characterized in that a sufficient number of codons which are poorly suited to yeasts is replaced with corresponding codons which are well-suited to yeasts in the said regions having a high content of codons which are poorly suited to yeasts.

Within the meaning of the present invention, "codons which are poorly suited to yeasts" are understood as being codons whose frequency of use by yeasts is less than or equal to approximately 13 per 1000, preferably less than or equal to approximately 12 per 1000, more preferably less than or equal to approximately 10 per 1000. The frequency at which codons are used by yeasts, more specifically by *S. cerevisiae*, is described, in particular, in "Codon usage data base from Yasukazu Nakamura" (http://www.dna.affrc.go.jp/~nakamura/codon.html). This applies, in particular, to codons CTC, CTG and CTT, which encode leucine, to codons CGG, CGC, CGA, CGT and AGG, which encode arginine, to codons GCG and GCC, which encode alanine, to codons GGG, GGC and GGA, which encode glycine, and to codons CCG and CCC, which encode proline. The codons which are poorly suited to yeasts in accordance with the invention are, more specifically, codons CTC and CTG, which encode leucine, CGG, CGC, CGA, CGT and AGG, which encode arginine, codons GCG and GCC, which encode alanine, GGG and GGC, which encode glycine, and codons CCG and CCC, which encode proline.

Within the meaning of the present invention, "corresponding codons which are well-suited to yeasts" are understood as being the codons which correspond to the codons which are poorly suited to yeasts and which encode the same amino acids, and whose frequency of use by yeasts is greater than 15 per 1000, preferably greater than or equal to 18 per 1000, more preferably greater than or equal to 20 per 1000. This applies, in particular, to codons TTG and TTA, preferably TTG, which encode leucine, to codon AGA, which encodes arginine, to codons GCT and GCA, preferably GCT, which encode alanine, to codon GGT, which encodes glycine, and to codon CCA, which encodes proline.

Within the meaning of the present invention, "region having a high content of codons which are poorly suited to yeasts" is understood as being any region of the DNA sequence which contains at least 2 poorly suited codons among 10 consecutive codons, with it being possible for the two codons to be adjacent or separated by up to 8 other codons. According to one preferred embodiment of the invention, the regions having a high content of poorly suited codons contain 2, 3, 4, 5 or 6 poorly suited codons per 10 consecutive codons, or contain at least 2 or 3 adjacent poorly suited codons.

Within the meaning of the present invention, "sufficient number of codons" is understood as being the number of codons which it is necessary and sufficient to replace in order to observe a substantial improvement in their expression in yeasts. Advantageously, at least 50% of the codons which are poorly suited to yeasts in the high-content region under consideration are replaced with well-suited codons. Preferably, at least 75% of the poorly suited codons of the said region are replaced, with 100% of the poorly suited codons more preferably being replaced.

Within the meaning of the present invention, "substantial improvement" is understood as being either a detectable expression when no expression of the reference sequence is observed, or an increase in expression as compared with the level at which the reference sequence is expressed.

Within the meaning of the present invention, "reference sequence" designates any sequence which encodes a protein of interest and which is modified in accordance with the invention in order to promote its expression in yeasts.

The present invention is particularly well suited to DNA sequences, in particular cDNA sequences, which encode proteins of interest which contain regions having a high content of leucine and in which a sufficient number of CTC codons encoding leucine in the said region having a high content of leucine is replaced with TTG and/or TTA codons, or in which a sufficient number of CTC and CTG codons encoding leucine in the said region having a high content of leucine is replaced with TTG and/or TTA codons, preferably with a TTG codon.

Within the meaning of the present invention, "region having a high content of leucine" is understood as being a region which contains at least 2 leucines among 10 consecutive amino acids in the protein of interest, with it being possible for the two leucines to be adjacent or separated by up to 8 other amino acids. According to one preferred embodiment of the invention, the regions having a high content of leucine contain 2, 3, 4, 5 or 6 leucines per 10 consecutive amino acids, or contain at least 2 or 3 adjacent leucines.

According to a preferred embodiment of the invention, at least 50% of the CTC or CTC and CTG codons of the region having a high content of leucine are replaced with TTG or TTA codons, with at least 75% of the CTC or CTC and CTG codons of the said region preferably being replaced, and 100% of the CTC or CTC and CTG codons more preferably being replaced.

Advantageously, the present invention is particularly suitable for DNA sequences whose general content of poorly suited codons is at least 20%, more preferably at least 30%, as compared with the total number of codons in the reference sequence.

Advantageously, when the reference sequence contains at least one 5' region having a high content of poorly suited codons, the recoding of this 5' region alone makes it possible to obtain a substantial improvement in the expression of the protein of interest in yeasts. The length of the 5' region to be recoded in accordance with the invention will vary depending on the length of the region having a high content of poorly suited codons. This length will advantageously be at least four codons, in particular when this region contains at least two adjacent poor codons, up to approximately 40 codons or more.

However, it is not necessary, according to the invention, to recode all the reference sequence, but only the regions having a high content of poor codons, in particular the 5' region on its own, in order to obtain a substantial improvement in the expression of the protein of interest in yeasts.

Advantageously, the DNA sequence encoding a protein of interest is an isolated DNA sequence of natural origin, in particular of plant origin. The invention is particularly advantageous for sequences which originate from monocotyledonous or dicotyledonous plants, preferably monocotyledonous plants, in particular of the graminae family, such as wheat, barley, oats, rice, maize, sorghum, cane sugar, etc.

According to a preferred embodiment of the invention, the DNA sequence encodes an enzyme, in particular a cytochrome P450, which is preferably of plant origin. These P450 cytochromes exhibit a high content of poorly suited codons, in particular encoding leucine, in their N-terminal region; it is in the 5'-terminal coding region that the poorly suited codons are replaced.

The present invention also relates to a chimeric gene which comprises a DNA sequence which has been modified as above and heterologous 5' and 3' regulatory elements which are able to function in a yeast, that is to say which are able to control the expression of the protein of interest in the yeast. Such regulatory elements are well known to the skilled person and are described, in particular, by Rozman et al. (Genomics, 38, 1996, 371–381) and by Nacken et al. (Gene, 175, 1996, 253–260, Probing the limits of expression levels by varying promoters strength and plasmid copy number in *Saccharomyces cerevisiae*).

The present invention also relates to a vector for transforming yeasts which contains at least one chimeric gene as described above. It also relates to a process for transforming yeasts with the said vector and to the transformed yeasts which are obtained. It finally relates to a process for producing a heterologous protein of interest in a transformed yeast, with the sequence which encodes the said protein of interest being such as defined above.

The process for producing a heterologous protein of interest in a transformed yeast comprising the steps of:

a) transforming a yeast with a vector which is able to replicate in yeasts and which contains a modified DNA sequence as defined above and heterologous 5' and 3' regulatory elements which are able to function in a yeast, b) culturing the transformed yeast, and c) extracting the protein of interest from the yeast culture.

When the protein of interest is an enzyme which is suitable for transforming a substrate, such as a cytochrome P450, the enzyme which has been extracted from the yeast culture is then used for catalysing the transformation of the said substrate.

However, the catalysis can be carried out, without requiring the extraction of the yeast, by culturing the transformed yeast in the presence of the said substrate.

The present invention also relates, therefore, to a process for transforming a substrate by enzymic catalysis using an enzyme which is expressed in a yeast, which process comprises the steps of a) culturing the yeast which has been transformed in accordance with the invention in the presence of the substrate to be transformed, then b) recovering the transformed substrate from the yeast culture.

When the yeast has been transformed for expressing a cytochrome P450, the reaction which is catalysed by the enzyme is an oxidation reaction, more specifically a reaction in which C—H or C═C bonds are oxidized.

The techniques for transforming and culturing yeasts are known to the skilled person, and are described, for example, in *Methods in Enzymology* (Vol. 194, 1991).

Yeasts which are of use in accordance with the invention are selected, in particular, from the genera Saccharomyces, Kluyveromyces, Hansenula, Pichia and Yarrowia. Advantageously, the yeast belongs to the Saccaromyces genus, and is in particular *S. cerevisiae.*

Other characteristics of the invention will become apparent in the light of the examples which follow.

EXAMPLE 1

Production of a Wheat cDNA Gene Library, and Identification of the CYP73A17 Sequence The wheat cytochrome P450 CYP73A17 sequence was obtained by screening a young wheat plantlet (shoots and roots without the caryopses) cDNA library which was constructed in the vector λ-ZapII (Stratagene) in accordance with the supplier's instructions.

1. Production of the cDNA Library

*Triticum aestivum* (L. cv. Darius) seeds which had been coated with cloquintacet-mexyl (0.1% per dry weight of seed) are cultured in plastic boxes on two layers of damp gauze until shoots having a size of 3 to 5 mm are obtained. The water in the boxes is then replaced with a solution of 4 mM sodium phenobarbital and the wheat is cultured until the shoots are approximately 1 cm in size.

The cDNA library is constructed in the λ-ZapII (Stratagene) vector, in accordance with the supplier's protocol and instructions, using 5 μg of poly(A)$^+$ RNA (Lesot, A., Benveniste, I., Hasenfratz, M. P., Durst, F. (1990) Induction of NADPH cytochrome P450(c) reductase in wounded tissues from *Helianthus tuberosus* tubers. Plant Cell Physiol., 31, 1177–1182) which were isolated from the treated roots and shoots.

2. Screening the cDNA Library

5×10$^5$ lysis plaques from the previously obtained λ-ZapII library are screened using a probe which corresponds to the complete coding sequence of *Helianthus tuberosus* CYP73A1, and which has been labelled by random priming with [α-$^{32}$P]dCTP. The filters are prehybridized and hybridized at low stringency at 55° C. in accordance with the standard protocols. The membranes are washed twice for 10 minutes with 2×SSC, 0.1% SDS, and once for 10 minutes with 0.2×SSC, 0.1% SDS at ambient temperature, then twice for 30 minutes with 0.2×SSC, 0.1% SDS at 45° C. The inserts of the positive lysis plaques are analysed by PCR (polymerization chain reaction) and hybridization in order to determine their size. The clones containing inserts which hybridize with CYP73A1 under the above-described conditions and which are greater than 1.5 kbp in size are rescreened before excision of the pBluescript plasmid in accordance with the supplier's (Stratagene) protocol and sequencing using the Ready Reaction Dye Deoxy Terminator Cycle prism technique developed by Applied Biosystems Inc. A full length clone is then identified by alignment with CYP73A1.

The wheat cytochrome P450 CYP73A17 which is encoded by the isolated sequence of SEQ ID NO: 1 (which encodes the amino acid sequence of SEQ ID NO: 15) exhibits 76.2% identity with the *Helianthus tuberosus* CYP73A1.

EXAMPLE 2

Alterations to the Sequence Encoding the Wheat Cytochrome P450 CYP73A17

Contrary to the situation with regard to *Helianthus tuberosus* CYP73A1, which can be expressed in yeasts (Urban et al., 1994), repeated attempts to express wheat CYP73A17 in yeasts using the same customary techniques proved to be fruitless when the nucleotide sequence was not altered at the time it was inserted into the expression vector (verification by sequencing). No protein is detected by spectrophotometry or by immunoblotting, just as no enzymic activity is detectable in the microsomes of transformed and induced yeast.

1. Alteration of the Coding Sequence

The sequence encoding wheat CYP73A17 (SEQ. ID No. 1) was therefore altered, in three different ways, by PCR-induced mutagenesis, as follows:

The BamHI and EcoRI restriction sites were respectively introduced by PCR just upstream of the ATG codon and just downstream of the stop codon of the CYP73A17 coding sequence (source, origin) using the sense and reverse primers described below, with the restriction sites being BamHI in the case of the sense primers Rec1 (SEQ ID No. 3), Rec2 (SEQ ID No. 4) and Rec3 (SEQ ID No. 5), and EcoRI in the case of the reverse primer (SEQ ID No. 6).

A primer, represented by SEQ ID No. 2, was also employed for enabling yeasts to be transformed with the unmodified (native) sequence encoding wheat CYP73A17.

The five primers described above were obtained from Eurogentech, and were synthesized and purified in accordance with customary methods.

For each alteration using the four different sense primers, the mode of operation is as follows:

The reaction mixture (20 mM Tris-HCl, pH 8.75, 10 mM KCl, 10 mM $(NH_4)_2SO_4$, 2 mM $MgSO_4$, 0.1% Triton×100, 0.1 mg/ml BSA, 5% (v/v) DMSO, 300 μM dNTP, 20 pmoles of each primer, 150 ng of template, total volume 50 μl ) is preheated at 94° C. for 2 minutes before adding 5 units of Pfu DNA polymerase (Stratagene). After 2 minutes at 94° C., 30 amplification cycles are carried out as follows: 1 minute of denaturation at 94° C., 2 minutes of hybridization at 55° C., 2 minutes of extension at 72° C. The reaction is completed by 10 minutes of extension at 72° C.

For each primer, a sequence is obtained which is derived from sequence ID No. 1, and which is represented, in the case of the altered coding sequences, by the sequences ID No. 7 (which encodes the amino acid sequence of SEQ. ID NO: 16), No. 8 (which encodes the amino acid sequence of SEQ. ID NO: 17), and No. 9 (which encodes the amino acid sequence of SEQ ID NO: 18). The 5' ends of the sequences obtained using the four above mentioned sense primers are depicted below, with the BamHI restriction site being shown in italics:

```
native: ATATATGGATCC ATG GAC GTC CTC CTC CTG GAG
Rec 1   ATATATGGATCC ATG GAT GTT TTG TTG TTG GAG
Rec 2   ATATATGGATCC ATG GAT GTT TTG TTG TTG GAA
Rec 3   ATATATGGATCC ATG GAT GTT TTG TTG TTG GAA
Protein:             met asp val leu leu leu glu

AAG GCC CTC CTG GGC CTC TTC GCC GCG GCG GTG CTG
AAG GCC CTC CTG GGC CTC TTC GCC GCG GCG GTG CTG
AAA GCT TTG TTG GGT TTG TTC GCC GCG GCG GTG CTG
AAA GCT TTG TTG GGT TTG TTT GCT GCT GCT GTT TTG
lys ala leu leu gly leu phe ala ala ala val leu

GCC ATC GCC GTC GCC AAG CTC ACC GGC AAG CGC TTC
GCC ATC GCC GTC GCC AAG CTC ACC GGC AAG CGC TTC
GCC ATC GCC GTC GCC AAG CTC ACC GGC AAG CGC TTC
GCT ATT GCT GTT GCT AAA TTG ACT GGT AAA AGA TTT
ala ile ala val ala lys leu thr gly lys arg phe

CGC CTC CCC CCT GGC CCC TCC GGC
CGC CTC CCC CCT GGC CCC TCC GGC
CGC CTC CCC CCT GGC CCC TCC GGC
AGA TTG CCA CCA GGT CCA TCC GGC
arg leu pro pro gly pro ser gly

GCC CCC ATC GTC ...
GCC CCC ATC GTC ...
GCC CCC ATC GTC ...
GCC CCC ATC GTC ...
ala pro ile val ...
```

2. Transforming the Yeasts

After having been digested with the restriction enzymes BamHI and EcoRI, the four above-described altered coding sequences are integrated into the vector pYeDP60, which is described by Pompon et al. (*Methods Enzymol*, 272, 1996, 51–64; WO 97/10344), the content of which is hereby incorporated by reference with regard to the plasmid, the method of insertion into the plasmid, and the method of transforming and growing the yeasts, in particular using the Saccharomyces cerevisiae yeast strains W(R), WAT21 and WAT11. The method for transforming and growing yeasts is also described by Pompon et al. and by Urban et al. (*Eur. J. Biochem*, 222, 1994, page 844, 2nd column, "Yeast transformation and cell culture").

4 transformed yeast strains, designated: W73A17(native), W73A17(Rec1), W73A17(Rec2) and W73A17(Rec3), are obtained.

EXAMPLE 3

Expression of CYP73A17 in the Altered Yeasts

The previously obtained transformed yeasts are cultured, in accordance with the method described by Urban et al. (*Eur. J. Biochem.*, 222, 1994, page 844, 2nd column, "Yeast transformation and cell culture"), in 50 ml of SGI medium at 30° C. for 72 h. The cells are recovered by centrifuging at 8000 g for 10 minutes, washed with 25 ml of YPI medium, recentrifuged, and then resuspended in 250 ml of YPI medium. The cells are induced with galactose for 14–16 h, while being shaken at 160 rpm, until the cell density reaches $10^8$ cells per ml. The microsomes are then prepared using the method described by Pierrel et al. (*Eur. J. Biochem.*, 224, 1994, 835–844).

The expression of CYP73A17 achieved in the case of the four strains is quantified by differential spectrophotometry using the method described by Omura and Sato (*J. Biol. Chem.*, 177, 678–693). It is proportional to the number of poorly suited codons which have been altered.

The microsomal enzymic activity is measured using the method described by Durst F., Benveniste I., Schalk M. and Werck-Reichhart D. (1996) Cinnamic acid hydroxylase activity in plant microsomes. Methods Enzymol. 272, 259–268. The results obtained after transforming WAT21 are recorded in the Table below. The activity is expressed as cinnamate 4-hydroxylase activity. The percentage additional activity (rounded values) illustrates the extent of the leap in activity which is observed after the poorly suited codons have been altered.

| Strain | Activity pmol/min/μg of protein | % additional activity |
|---|---|---|
| W73A17 native | 0.64 | — |
| W73A17 Rec1 | 2.84 | +340 |
| W73A17 Rec2 | 4.92 | +670 |
| W73A17 Rec3 | 8.90 | +1300 |

These results relating to the increase in enzymic activity confirm those relating to the increase in the expression of the protein in the yeasts. They demonstrate that alteration of the 5' end alone, even when limited (Rec1), is sufficient to obtain a very substantial improvement in the production of the enzyme by the yeast and in its enzymic activity.

EXAMPLE 4

Expression of Wheat CYP86A5 in the Altered Yeasts

The sequence encoding wheat cytochrome P450 wheat CYP86A5, which is depicted by sequence identifier No. 10, which encodes the amino acid sequence of SEQ ID NO: 19 (SEQ ID No. 10), was isolated from the wheat cDNA library described in Example 1 using the same method of operation as described for the CYP73A17 sequence and employing the complete coding sequence of *Arabidopsis thaliana* CYP86A1 as the probe. This wheat CYP86A5 sequence was altered, in accordance with the mode of operation of Example 2, using the two oligonucleotides depicted by the sequences ID No. 12 and 13 (SEQ ID No. 12 and SEQ ID No. 13) as sense and reverse primers, respectively, in order to obtain the coding sequence which is altered in accordance with the invention and which is depicted by sequence identifier No. 14, which encodes the amino acid sequence of SEQ ID NO: 20 (SEQ ID No. 14).

A primer depicted by SEQ ID No. 11 was also used to enable yeasts to be transformed with the sequence encoding unmodified (native) wheat CYP86A5.

The yeasts are transformed with this new coding sequence and the expression is quantified by differential spectrophotometry in accordance with the mode of operation described in Example 2. While the natural sequence of wheat CYP86A5 is not expressed in a detectable manner, there is substantial expression in the transformed yeasts of the sequence which has been modified in accordance with the invention.

The above-described examples demonstrate unambiguously that the expression in yeasts of DNA sequences which possess a 5' region having a high content of codons which are poorly suited to yeasts is substantially improved when this region alone is simply recoded in accordance with the invention, ever partially, with corresponding codons which are well-suited to yeasts.

What is claimed is:

1. A method of producing a protein in yeast comprising:

(a) selecting a protein encoded by a reference DNA sequence that comprises at least one region of ten consecutive codons comprising at least two codons that have a first frequency of use by yeast of less than or equal to 13 per 1000 codons;

(b) replacing at least 50% of codons that have a first frequency of use codons in the reference DNA sequence with having a second frequency of use by yeast of greater than or equal to 15 per 1000 codons and encoding the same amino acid as the codon being replaced to provide a modified sequence;

(c) transforming yeast with a vector comprising said modified sequence under the control of yeast regulatory elements; and (d) culturing said transformed yeast under conditions whereby said modified sequence is expressed to provide said protein.

2. The method of claim 1 wherein said first frequency of use is less than or equal to 12 per 1000 codons.

3. The method of claim 1 wherein said first frequency of use is less than or equal to 10 per 1000 codons.

4. The method of claim 1 wherein said codons having said first frequency of use are each independently selected from the group consisting of CTC, CTG and CTT encoding leucine, CGG, CGC, CGA, CGT and AGG encoding arginine, GCG and GCC encoding alanine, GGG, GGC and GGA encoding glycine and CCG and CCC encoding proline.

5. The method of claim 1 wherein said codons having said first frequency of use are each independently selected from the group consisting of CTC and CTG encoding leucine, CGG, CGC, CGA, CGT and AGG encoding arginine, GCG and GCC encoding alanine, GGG and GGC encoding glycine and CCG and CCC encoding proline.

6. The method of claim 1 wherein said second frequency of use is greater than or equal to 18 per 1000 codons.

7. The method of claim 1 wherein said second frequency of use is greater than or equal to 20 per 1000 codons.

8. The method of claim 1 wherein said region of ten consecutive codons comprises at least three codons that have a first frequency of use by yeast of less than or equal to 13 per 1000 codons.

9. The method of claim 1 wherein said region of ten consecutive codons comprises at least four codons that have a first frequency of use by yeast of less than or equal 13 per 1000 codons.

10. The method of claim 1 wherein said region of ten consecutive codons comprises at least five codons that have a first frequency of use by yeast of less than or equal to 13 per 1000 codons.

11. The method of claim 1 wherein said region of ten consecutive codons comprises at least six codons that have a first frequency of use by yeast of less than or equal to 13 per 1000 codons.

12. The method of claim 4 wherein at least 50% of said codons that have a first frequency of use are replaced, the replacement selected from CTC, CTG or CTT replaced by a codon independently selected from TTG and TTA; CGG, CGC, CGA, CGT or AGG replaced by AGA; GCG or GCC replaced by a codon independently selected from GCT and GCA; GGG, GGC or GGA replaced by GGT; and CCG or CCC replaced by CCA.

13. The method of any one of claims 1 and 8–11 wherein at least two of said codons that have a first frequency of use are adjacent.

14. The method of any one of claims 8–11 wherein at least three of said codons that have a first frequency of use are adjacent.

15. A method of producing a protein in yeast comprising:

(a) selecting a protein encoded by a reference DNA sequence that has at least one region of ten consecutive codons comprising at least two codons encoding leucine and independently selected from CTC and CTG;

(b) replacing at least 50% of said codons encoding leucine by a codon independently selected from the group consisting of TTG and TTA to provide a modified sequence;

(c) transforming yeast with a vector comprising said modified sequence under the control of yeast regulatory elements; and (d) culturing said transformed yeast under conditions whereby said modified sequence is expressed to provided said protein.

16. The method of claim 15 wherein at least 50% of said CTC and CTG codons are replaced by TTG.

17. The method of claim 15 wherein said region of ten consecutive codons comprises at least three codons encoding leucine and independently selected from CTC and CTG.

18. The method of claim 15 wherein said region of ten consecutive codons comprises at least four codons encoding leucine and independently selected from CTC and CTG.

19. The method of claim 15 wherein said region of ten consecutive codons comprises at least five codons encoding leucine and independently selected from CTC and CTG.

20. The method of claim 15 wherein said region of ten consecutive codons comprises at least six codons encoding leucine and independently selected from CTC and CTG.

21. The method of claim 1 or 15, wherein at least 20% of the total codons of said reference DNA sequence are codons that have a frequency of use by yeast of less than or equal to 13 per 1000 codons.

22. The method of claim 1 or 15, wherein at least 30% of the total codons of said reference DNA sequence are codons that have a frequency of use by yeast of less than or equal to 13 per 1000 codons.

23. The method of claim 1 or 15, wherein said region of ten consecutive codons is in the 5' region of said reference DNA sequence.

24. The method of claim 1 or 15, wherein said reference DNA sequence is of plant origin.

25. The method of claim 1 or 15, wherein said protein is an enzyme.

26. The method of claim 1 or 15, wherein said protein is cytochrome P450.

27. The method of claim 1 or 15, wherein said yeast is selected from the group consisting of Saccharomyces, Kluveromyces, Hansenula, Pichici and Yartowia.

28. The method of claim 1 or 15, wherein said yeast is *S. cerevisiae.*

29. The method of claim 24 wherein said plant is a monocot.

30. The method of claim 24, wherein said plant is selected from the group consisting of wheat, barley, oats, rice, maize, sorghum and cane sugar.

31. The method of claim 26, wherein said reference DNA sequence comprises SEQ ID NO: 1 or 10.

32. The method of claim 26, wherein said modified DNA sequence comprises SEQ ID NO: 7, 8, 9 or 14.

33. A method of producing a protein in yeast comprising:

(a) selecting a protein encoded by a reference DNA sequence that comprises at least one region of ten consecutive codons comprising at least two codons independently selected from the group consisting of CTC, CTG and CTT encoding leucine, CGG, CGC, CGA, CGT and AGG encoding arginine, GCG and GCC encoding alanine, GGG, GGC and GGA encoding glycine, and CCG and CCC encoding proline;

(b) replacing at least 50% of codons in one region of ten consecutive codons, the replacement being selected from CTC, CTG and CTT replaced by a codon independently selected from TTG and TTA; CGG, CGC, CGA, CGT and AGG replaced by AGA; GCG and GCC replaced by a codon independently selected from GCT and GCA; GGG, GGC and GGA replaced by GGT; and CCG and CCC replaced by CCA.

34. A method of preparing a DNA sequence having improved translation in yeast comprising:

(a) selecting a protein encoded by a reference DNA sequence that comprises at least one region of ten consecutive codons comprising at least two codons that have a first frequency of use by yeast of less than or equal to 13 per 1000 codons;

(b) replacing at least 50% of codons that have a first frequency of use of the reference DNA sequence by codons having a second frequency of use by yeast of greater than or equal to 15 per 1000 codons and encoding the same amino acid as the codon being replaced.

35. The method of claim 34 wherein said first frequency of use is less than or equal to 12 per 1000 codons.

36. The method of claim 34 wherein said first frequency of use is less than or equal to 10 per 1000 codons.

37. The method of claim 34 wherein said codons having said first frequency of use are each independently selected from the group consisting of CTC, CTG and CTT encoding leucine, CGG, CGC, CGA, CGT and AGG encoding arginine, GCG and GCC encoding alanine, GGG, GGC and GGA encoding glycine and CCG and CCC encoding proline.

38. The method of claim 34 wherein said codons having said first frequency of use are each independently selected from the group consisting of CTC and CTG encoding leucine, CGG, CGC, CGA, CGT and AGG encoding arginine, GCG and GCC encoding alanine, GGG and GGC encoding glycine and CCG and CCC encoding proline.

39. The method of claim 34 wherein said second frequency of use is greater than or equal to 18 per 1000 codons.

40. The method of claim 34 wherein said second frequency of use is greater than or equal to 20 per 1000 codons.

41. The method of claim 34 wherein said region of ten consecutive codons comprises at least four codons that have a first frequency of use by yeast of less than or equal 13 per 1000 codons.

42. The method of claim 34 wherein said region of ten consecutive codons comprises at least five codons that have a first frequency of use by yeast of less than or equal to 13 per 1000 codons.

43. The method of claim 34 wherein said region often consecutive codons comprises at least six codons that have a first frequency of use by yeast of less than or equal to 13 per 1000 codons.

44. The method of claim 35 wherein at least 50% of said codons that have a first frequency of use are replaced, the replacement selected from CTC, CTG or CTT replaced by a codon independently selected from TTG and TTA; CGG, CGC, CGA, CGT or AGG replaced by AGA; GCG or GCC replaced by a codon independently selected from GCT and GCA; GGG, GGC or GGA replaced by GGT; and CCG or CCC replaced by CCA.

45. The method of claim 35 wherein said region of ten consecutive codons comprises at least three codons that have a first frequency of use by yeast of less than or equal to 13 per 1000 codons.

46. The method of any one of claims 34, 41–43 and 45 wherein at least two of said codons that have a first frequency of use are adjacent.

47. The method of any one of claims 41–43 and 45 wherein at least three of said codons that have a first frequency of use are adjacent.

* * * * *

UNITED STATES PATENT AND TRADEMARK OFFICE

CERTIFICATE OF CORRECTION

PATENT NO. : 6,180,363 B1
DATED : January 30, 2001
INVENTOR(S) : Batard et al.

It is certified that error appears in the above-identified patent and that said Letters Patent is hereby corrected as shown below:

Title page,
Item [73], Assignee, "Cede" should read -- Cedex --
Item [75], Inventor(s), "Dingscheim," should read -- Dungscheim, --

Column 1,
Line 27, "C—II" should read -- C—H --

Column 37,
Line 49, "codons" should be deleted
Line 50, "with having" should read -- with codons having --

Column 39,
Line 52, "vided" should read -- vide --
Line 64, "Sacchoromyces," should read -- *Sacchoromyces*, --
Line 65, "Kluveromyces," should read -- Kluyveromyces, --; "Hansenula," should read -- *Hansenula*, --; "Pichici" should read -- *Pichici* --; and "Yartowia." should read -- *Yarrowia.* --

Column 40,
Line 34, "of" (second occurrence) should read -- in --

Column 41,
Line 1, "often" should read -- of ten --

Signed and Sealed this

Twenty-seventh Day of August, 2002

*Attest:*

JAMES E. ROGAN

*Attesting Officer*

*Director of the United States Patent and Trademark Office*